US011864730B2

(12) United States Patent
Patel et al.

(10) Patent No.: US 11,864,730 B2
(45) Date of Patent: Jan. 9, 2024

(54) SYSTEMS, APPARATUSES, AND METHODS FOR ENDOSCOPY

(71) Applicant: Endoluxe Inc., Dunwoody, GA (US)

(72) Inventors: Neal Patel, Dunwoody, GA (US); Philip Zhao, Dunwoody, GA (US); Devon Bream, Dunwoody, GA (US)

(73) Assignee: Endoluxe Inc., Allentown, PA (US)

(*) Notice: Subject to any disclaimer, the term of this patent is extended or adjusted under 35 U.S.C. 154(b) by 0 days.

(21) Appl. No.: 18/103,022

(22) Filed: Jan. 30, 2023

(65) Prior Publication Data

US 2023/0248211 A1 Aug. 10, 2023

Related U.S. Application Data

(63) Continuation of application No. 17/572,332, filed on Jan. 10, 2022.

(51) Int. Cl.
*A61B 1/00* (2006.01)
*G16H 20/40* (2018.01)
(Continued)

(52) U.S. Cl.
CPC ........ *A61B 1/0005* (2013.01); *A61B 1/00052* (2013.01); *A61B 1/000094* (2022.02);
(Continued)

(58) Field of Classification Search
CPC ........ A61B 1/000094; A61B 1/000096; A61B 1/0005; A61B 1/00052; A61B 1/307; A61B 1/00045; A61B 1/00009
See application file for complete search history.

(56) References Cited

U.S. PATENT DOCUMENTS

| 4,478,212 A | 10/1984 | Asano |
| 5,311,859 A | 5/1994 | Monroe et al. |

(Continued)

FOREIGN PATENT DOCUMENTS

| WO | WO2015191954 | 12/2015 |
| WO | 2019246580 A1 | 12/2019 |

(Continued)

OTHER PUBLICATIONS

International Search Report and Written Opinion dated Sep. 18, 2015 in related PCT Application No. PCT/US15/35479 filed Jun. 12, 2015 (7 pages).

(Continued)

*Primary Examiner* — Aaron B Fairchild
(74) *Attorney, Agent, or Firm* — Dentons US LLP

(57) ABSTRACT

A portable endoscopic system comprising an imaging unit for an endoscopic procedure. The imaging unit has an imaging coupler for receiving imaging information from an imaging assembly of an endoscope; a display integrated into a housing of the imaging unit; an image processing unit for processing the received imaging information into images of a time series and to displaying the image in real-time; a motion sensor configured to detect a motion of the housing; and a detection processing unit. The detection processing unit is configured to classify at least one anatomical feature in each image of the time series based on an artificial intelligence classifier; determine a confidence metric of the classification; determine a motion vector based on the detected motion; and display, concurrently with the corresponding image, the classification of the at least one anatomical feature, the determined confidence metric, and the determined motion vector.

30 Claims, 8 Drawing Sheets

(51) Int. Cl.
*G16H 30/40* (2018.01)
*G16H 40/63* (2018.01)
*A61B 1/307* (2006.01)
*A61B 5/06* (2006.01)
*G06T 7/00* (2017.01)

(52) U.S. Cl.
CPC ........ *A61B 1/000096* (2022.02); *A61B 1/307* (2013.01); *A61B 5/067* (2013.01); *G06T 7/0014* (2013.01); *G16H 20/40* (2018.01); *G16H 30/40* (2018.01); *G16H 40/63* (2018.01); *G06T 2207/10016* (2013.01); *G06T 2207/10068* (2013.01); *G06T 2207/20084* (2013.01); *G06T 2207/30081* (2013.01)

(56) References Cited

U.S. PATENT DOCUMENTS

| | | | |
|---|---|---|---|
| 5,808,813 A | 9/1998 | Lucey et al. | |
| 5,822,546 A | 10/1998 | George | |
| 6,646,866 B2 | 11/2003 | Kao | |
| 6,657,654 B2 | 12/2003 | Narayanaswami | |
| 7,442,167 B2 | 10/2008 | Dunki-Jacobs et al. | |
| 7,986,342 B2 | 7/2011 | Yogesan et al. | |
| 8,029,439 B2 | 10/2011 | Todd et al. | |
| 8,604,753 B2 | 12/2013 | Bessa et al. | |
| 8,711,552 B2 | 4/2014 | Medica et al. | |
| D710,856 S | 8/2014 | Daniel | |
| 8,928,746 B1 | 1/2015 | Stevrin et al. | |
| 8,944,596 B2 | 2/2015 | Wood et al. | |
| 10,051,166 B2 | 8/2018 | Duckett, III et al. | |
| 2002/0103420 A1 | 8/2002 | Coleman et al. | |
| 2003/0050534 A1 | 3/2003 | Kazakevich | |
| 2003/0227746 A1 | 12/2003 | Sato | |
| 2004/0037454 A1* | 2/2004 | Ozawa | A61B 1/0669 382/128 |
| 2004/0225223 A1* | 11/2004 | Honda | A61B 1/041 128/920 |
| 2005/0191046 A1 | 9/2005 | Dehmel et al. | |
| 2006/0116550 A1 | 6/2006 | Noguchi et al. | |
| 2006/0215013 A1 | 9/2006 | Jongsma et al. | |
| 2007/0195165 A1* | 8/2007 | Hirakawa | A61B 1/0005 348/75 |
| 2007/0268280 A1* | 11/2007 | Fujita | A61B 1/00045 345/204 |
| 2008/0104300 A1 | 5/2008 | Diener et al. | |
| 2008/0183910 A1 | 7/2008 | Natoli et al. | |
| 2008/0207996 A1 | 8/2008 | Tsai | |
| 2009/0012361 A1 | 1/2009 | MacKinnon et al. | |
| 2009/0027486 A1* | 1/2009 | Hirakawa | A61B 1/0005 348/45 |
| 2009/0051695 A1* | 2/2009 | Matsuda | G06T 7/0012 345/556 |
| 2009/0186264 A1 | 7/2009 | Huang | |
| 2010/0097392 A1* | 4/2010 | Nishiyama | A61B 1/041 345/635 |
| 2010/0145146 A1 | 6/2010 | Melder | |
| 2010/0198009 A1 | 8/2010 | Farr et al. | |
| 2010/0279418 A1 | 11/2010 | Larson et al. | |
| 2011/0015496 A1 | 1/2011 | Sherman et al. | |
| 2011/0055447 A1 | 3/2011 | Costa | |
| 2011/0195753 A1 | 8/2011 | Mock et al. | |
| 2011/0196201 A1* | 8/2011 | Sato | A61B 1/00016 600/109 |
| 2012/0077552 A1 | 3/2012 | Bessa et al. | |
| 2012/0106037 A1 | 5/2012 | Diebel et al. | |
| 2012/0162401 A1* | 6/2012 | Melder | H04N 7/183 348/E7.085 |
| 2012/0225622 A1 | 9/2012 | Kudrna et al. | |
| 2012/0238810 A1* | 9/2012 | Kobayashi | A61B 1/000095 600/109 |
| 2012/0320340 A1 | 12/2012 | Coleman | |
| 2013/0083185 A1 | 4/2013 | Coleman | |
| 2013/0096378 A1 | 4/2013 | Alexander et al. | |
| 2013/0102359 A1 | 4/2013 | Ho | |
| 2013/0262730 A1 | 10/2013 | Al-Ali et al. | |
| 2013/0281155 A1 | 10/2013 | Ogata et al. | |
| 2013/0344917 A1 | 12/2013 | Sobti et al. | |
| 2014/0038222 A1 | 2/2014 | Alt et al. | |
| 2014/0051923 A1 | 2/2014 | Mirza et al. | |
| 2014/0073969 A1 | 3/2014 | Zou et al. | |
| 2014/0107416 A1 | 4/2014 | Birnkrant | |
| 2014/0140049 A1 | 5/2014 | Cotelo | |
| 2014/0142390 A1 | 5/2014 | Bromwich | |
| 2014/0170761 A1 | 6/2014 | Crawford et al. | |
| 2014/0192492 A1 | 7/2014 | Wojcik et al. | |
| 2014/0200054 A1 | 7/2014 | Fraden | |
| 2014/0210977 A1 | 7/2014 | Amling et al. | |
| 2014/0249405 A1 | 9/2014 | Wimer | |
| 2014/0364711 A1 | 12/2014 | Ismail et al. | |
| 2015/0002606 A1 | 1/2015 | Hyde et al. | |
| 2015/0073285 A1 | 3/2015 | Albert et al. | |
| 2015/0112141 A1 | 4/2015 | Storz | |
| 2015/0254072 A1 | 9/2015 | Wojcik et al. | |
| 2015/0362828 A1 | 12/2015 | Patel et al. | |
| 2015/0381887 A1 | 12/2015 | Sato et al. | |
| 2017/0099479 A1 | 4/2017 | Browd et al. | |
| 2017/0273539 A1 | 9/2017 | Law et al. | |
| 2019/0167074 A1 | 6/2019 | Malinskiy et al. | |

FOREIGN PATENT DOCUMENTS

| | | |
|---|---|---|
| WO | 2020257533 A1 | 12/2020 |
| WO | 2021194872 A1 | 9/2021 |

OTHER PUBLICATIONS

International Search Report and Written Opinion dated Jan. 17, 2019 in related PCT Application No. PCT/US18/58357 filed Oct. 31, 2018 (13 pages).

International Search Report for PCT/US2023/010457 dated Apr. 17, 2023, 21 pages.

* cited by examiner

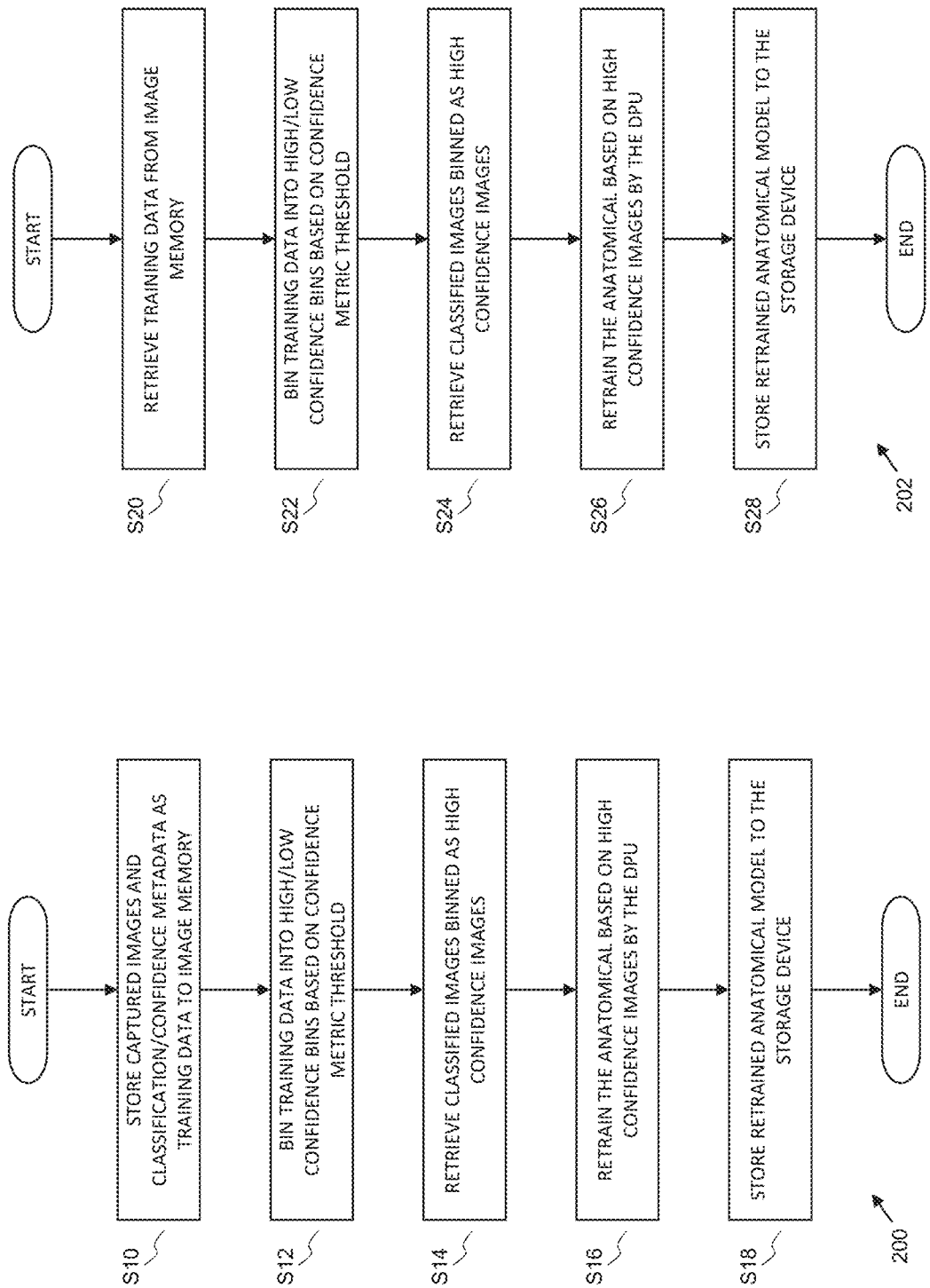

SYSTEMS, APPARATUSES, AND METHODS FOR ENDOSCOPY

CROSS-REFERENCE TO RELATED PATENT APPLICATION

This patent application is a continuation of U.S. patent application Ser. No. 17/572,332 filed 10 Jan. 2022, which is incorporated by reference herein for all purposes.

TECHNICAL FIELD

The present disclosure relates to systems, apparatuses, and methods utilizing an endoscopic imaging system. More specifically, the present disclosure relates to systems, apparatuses, and methods utilizing an endoscopic system for enabling various endoscopic procedures (medical and non-medical). For example, various technologies disclosed herein enable prevention, forecasting, diagnosis, amelioration, monitoring, or treatment of medical conditions in various mammalian pathology, such as human prostate pathology including but not limited to benign prostatic hyperplasia (BPH) or other human or non-human medical conditions, or non-medical procedures.

BACKGROUND

There are various prostate diseases. One of those is benign prostatic hyperplasia (BPH), which may be found in nearly every aging human male. BPH is often the primary cause for lower urinary tract symptoms (LUTS), such as nocturia, frequency, urgency, hesitancy, incomplete emptying, leakage, and dribbling. It is generally estimated that 90% of men between the ages of 45 and 80 years have some form of LUTS or BPH with prevalence increasing nearly linearly with age. While BPH is rarely life-threatening, BPH can lead to numerous clinical conditions including urinary retention, renal insufficiency, recurrent urinary tract infections, incontinence, hematuria, and bladder stones. Thus, early intervention may sometimes be recommended to improve patient outcomes and quality of life.

Although several drug therapies are available and effective to treat BPH, their effectiveness is typically short-lived. Surgical treatments for BPH range from minimally invasive techniques, such as prostatic urethral lift devices and various ablation methods, to more invasive resection surgeries to fully invasive prostatectomy surgeries. The surgeries involve cutting or ablating tissue near delicate structures, such as the bladder and the verumontanum, which is critical for male sexual function. Therefore, these surgeries require extensive practice with cystoscopic methods to identify the delicate structures and to estimate the treatment areas proximate to those delicate structures.

Minimally invasive procedures offer the advantage of less pain, faster recovery, lower costs, and the use of local anesthesia and mild sedation. Transurethral prostatic procedures involve tissue examination of the bladder and urethral mucosa with a specialty endoscope called a cystoscope. During an examination, a physician will expand the urethra and bladder with a clear fluid to visualize the mucosal surface of the bladder and urethra. For prostatic procedures, typically the region distal to the bladder neck and proximal to the verumontanum are identified as the treatment area. Once the treatment area is identified, the physician can apply treatment to one or more of the lateral, medial, and anterior prostatic lobes.

Ablative or respective prostatic surgeries require highly-specialized equipment, such as microwave, ultrasound, laser, vapor, or cryotherapy sources that provide ablative energy to a purpose-built therapeutic device. Furthermore, transurethral ablative procedures tend to be expensive and/or complicative due to their specialized equipment and need for technical expertise and thus not practical in ambulatory/office settings or in areas of the world where such equipment are cost-prohibitive. Recently, transurethral water vapor therapies (TWVT) have gained momentum as a treatment modality with good efficacy for large prostate volumes. Prostatic urethral lift (PUL) procedures have also become a mainstay of BPH treatment in the past decade preserving ejaculatory function, while requiring minimal anesthesia. Patients that received a PUL procedure reported generally better sexual function, improved recovery time, and less interference in daily activities over other treatment modalities. PUL devices are permanent, implantable fixation devices similar to tacks or anchors that aim to create channels in one or more of the prostatic lobes between the bladder neck to the verumontanum to reduce obstruction and improve flow.

Despite the treatment modality, each requires accurate localization to achieve optimal and enduring results. For example, in a PUL procedure typically four to five implants are required for an average-sized prostate to achieve an ideal opening, but upwards of ten implants may be necessary for large and/or abnormally shaped prostates. The first implant is placed approximately 2 cm distally of the bladder neck, the second implant placed just anterior to the verumontanum, with additional implants placed in between to form a continuous channel typically through the anterior and lateral aspects of the prostate. Each implant is housed in a disposable cartridge that must be replaced after the implant is deployed. Thus, the effector handle, cartridge, cystoscope are removed to replace the cartridge and introduce a new implant. While the sheath remains disposed in the prostatic urethra, the physician must constantly iterate this process, which can introduce errors in the optimal placement of implants. Furthermore, many of the PUL devices require the physician to actuate one or more controls multiple times to fully deploy the implant thereby further exacerbating achievement of optimal implantation. Finally, identifying the optimal location of the implants based on each patient's unique anatomy requires a learning curve that can be highly subjective.

These compromises and technological problems are believed to be present in virtually all currently known treatment modalities for typical prostate pathologies and not just PUL-type treatments. Accordingly, there exists a technological need for a lightweight, portable imaging platform for endoscopic therapies to identify and track anatomical landmarks and therapeutic sites in vivo.

BRIEF SUMMARY

This disclosure addresses these compromises and solves the technological problems noted above by enabling various systems, apparatuses, and methods for endoscopy, whether for medical (e.g., prevention, forecasting, diagnosis, amelioration, monitoring, or treatment of medical conditions in various mammalian pathology) or non-medical purposes (e.g., to assist visual inspection of narrow, difficult-to-reach cavities). These and other features, aspects, and advantages of the present embodiments will become better understood upon consideration of the following detailed description, drawings, and appended claims.

In one example of the present disclosure, an imaging unit for an endoscopic procedure is presented. The imaging unit comprises a housing and a display integrated into the housing. An imaging coupler is configured for receiving imaging information from an imaging assembly of an endoscope having a field of view (FoV) comprising of at least a portion of an end effector and a portion of a region of interest (ROI). An imaging processor is configured with instructions to process the received imaging information into pixel values representing an image of a time series and to display the image in real-time on the display, while a motion sensor is configured to detect a motion of the housing during the time series. The imaging unit comprises a detection processing unit (DPU) configured with instructions to: classify at least one anatomical feature in each image of the time series based on an artificial intelligence classifier; determine a confidence metric of the classification; determine a motion vector based on the detected motion; and display, concurrently with the corresponding image, the classification of the at least one anatomical feature, the determined confidence metric, and the determined motion vector.

In another example of the present disclosure, the motion sensor includes at least a gyroscope configured to generate a gyroscopic signal and an accelerometer configured to generate acceleration signals, the detection processing unit further configured to determine a displacement vector based on at least the gyroscopic signal and the acceleration signal.

In another example of the present disclosure, the DPU is configured to display the displacement vector concurrently with the corresponding classification In another example of the present disclosure, the detection processing unit is configured to display the displacement vector relative to one or more classified anatomical features.

In another example of the present disclosure, the detection processing unit is configured to display a plurality of displacement vectors each one relative to a unique classified anatomical feature.

In another example of the present disclosure, wherein the artificial intelligence classifier is a convolutional neural network configured to compare each image to an anatomical model.

In another example of the present disclosure, wherein the detection processing unit determines the confidence metric based on the comparison.

In another example of the present disclosure, the detection processing unit is configured to identify at least one treatment site based on the at least one classified anatomical feature, and display, concurrently with the corresponding image, the at least one identified treatment site and a relative motion vector between the classified anatomical feature and the identified treatment site.

In another example of the present disclosure, the region of the interest includes at least a prostatic urethra the administered therapy includes prostatic treatment, the detection processing unit is further configured to classify a prostatic pathology.

In another example of the present disclosure, a method for endoscopic imaging is presented. The method includes operatively coupling an imaging coupler of an imaging unit to an observation port of an endoscope. Imaging information is received from an imaging assembly of the endoscope. The imaging assembly has an FoV comprising of at least a portion of an end effector and a portion of a ROI. The received imaging information is processed into pixel values representing an image of a time series. The images are displayed in real-time on a display integrated into the housing of the imaging unit, and motion of the housing is detected during the capture of the time series. At least one anatomical feature is classified in each image of the time series based on an artificial intelligence classifier. A confidence metric of the classification is determined; a motion vector based on the detected motion is determined; and, concurrently with the corresponding image, the classification of the at least one anatomical feature, the determined confidence metric, and the determined motion vector are displayed on the display in real-time.

In another example of the present disclosure, wherein the step of detecting motion further includes generating a gyroscopic and acceleration signal associated with the motion of the housing. A displacement vector based on at least the gyroscopic signal and the acceleration signal is determined.

In another example of the present disclosure, wherein the method further includes displaying the displacement vector concurrently with the corresponding classification.

In another example of the present disclosure, wherein the method further includes displaying the displacement vector relative to one or more classified anatomical features.

In another example of the present disclosure, wherein the method further includes displaying a plurality of displacement vectors each one relative to a unique classified anatomical feature In another example of the present disclosure, wherein the artificial intelligence classifier is a convolutional neural network configured to compare each image to an anatomical model.

In another example of the present disclosure, wherein the confidence metric is based on the comparison.

In another example of the present disclosure, wherein the method further includes identifying at least one treatment site based on the at least one classified anatomical feature; and displaying, concurrently with the corresponding image, the at least one identified treatment site and the determined motion vector.

In another example of the present disclosure, wherein the region of the interest includes at least a prostatic urethra and the administered therapy includes prostatic treatment, the method further includes classifying a prostatic pathology.

In another example of the present disclosure, a kit for an endoscopic therapeutic procedure is presented. The kit includes an endoscopic imaging unit which comprises a housing and a display integrated into the housing. The endoscopic imaging unit includes an imaging coupler is configured for receiving imaging information from an imaging assembly of an endoscope having a field of view (FoV) comprising of at least a portion of an end effector and a portion of a region of interest (ROI). In addition, the endoscopic imaging unit includes an imaging processor; a motion sensor configured to detect a motion of the housing during the time series; and a detection processing unit (DPU). Furthermore, the kit includes instructions to perform a method for endoscopic imaging. The method includes the steps of: operatively coupling the imaging coupler of the imaging unit to an observation port of an endoscope; receiving the imaging information from the imaging assembly; processing the received imaging information into pixel values representing an image of a time series; displaying the image in real-time on the display; detecting motion of the housing during the time series; classifying at least one anatomical feature in each image of the time series based on an artificial intelligence classifier; determining a confidence metric of the classification; determining a motion vector based on the detected motion; and displaying, concurrently with the corresponding image, the classification of the at least one anatomical feature, the determined confidence metric, and the determined motion vector.

In another example of the present disclosure, wherein the step of detecting motion further includes generating a gyroscopic and acceleration signal associated with the motion of the housing, and determining a displacement vector based on at least the gyroscopic signal and the acceleration signal. Wherein the artificial intelligence classifier is a convolutional neural network configured to compare each image to an anatomical model.

In an embodiment, a method may comprise: receiving, by a processor, an imagery from an endoscope imaging a cavity, wherein the imagery depicts an anatomical feature within the cavity; performing, by the processor, a classification for the anatomical feature while the endoscope images the cavity; determining, by the processor, a confidence metric for the classification while the endoscope images the cavity; determining, by the processor, a motion vector for the endoscope imaging the cavity while the endoscope images the cavity; and requesting, by the processor, a display to simultaneously present at least two of the imagery, the classification, the confidence metric, or the motion vector while the endoscope images the cavity.

In an embodiment, a method may comprise: receiving, by a processor, an imagery from an endoscope imaging a cavity, wherein the imagery depicts an anatomical feature within the cavity; performing, by the processor, a classification for the anatomical feature while the endoscope images the cavity; determining, by the processor, a confidence metric for the classification while the endoscope images the cavity; determining, by the processor, a motion vector for the endoscope imaging the cavity while the endoscope images the cavity; and taking, by the processor, an action based on the classification, the confidence metric, and the motion vector.

DESCRIPTION OF DRAWINGS

In order that the manner in which the above-recited and other advantages and objects of the disclosure are obtained, a more particular description of the disclosure briefly described above will be rendered by reference to a specific embodiment thereof which is illustrated in the appended drawings. Understanding that these drawings depict only a typical embodiment of the disclosure and are not, therefore, to be considered to be limiting of its scope, the disclosure will be described and explained with additional specificity and detail through the use of the accompanying drawings in which:

FIGS. 6A-6B are flowcharts of embodiments for training an anatomical model;

DETAILED DESCRIPTION

Figure 1:
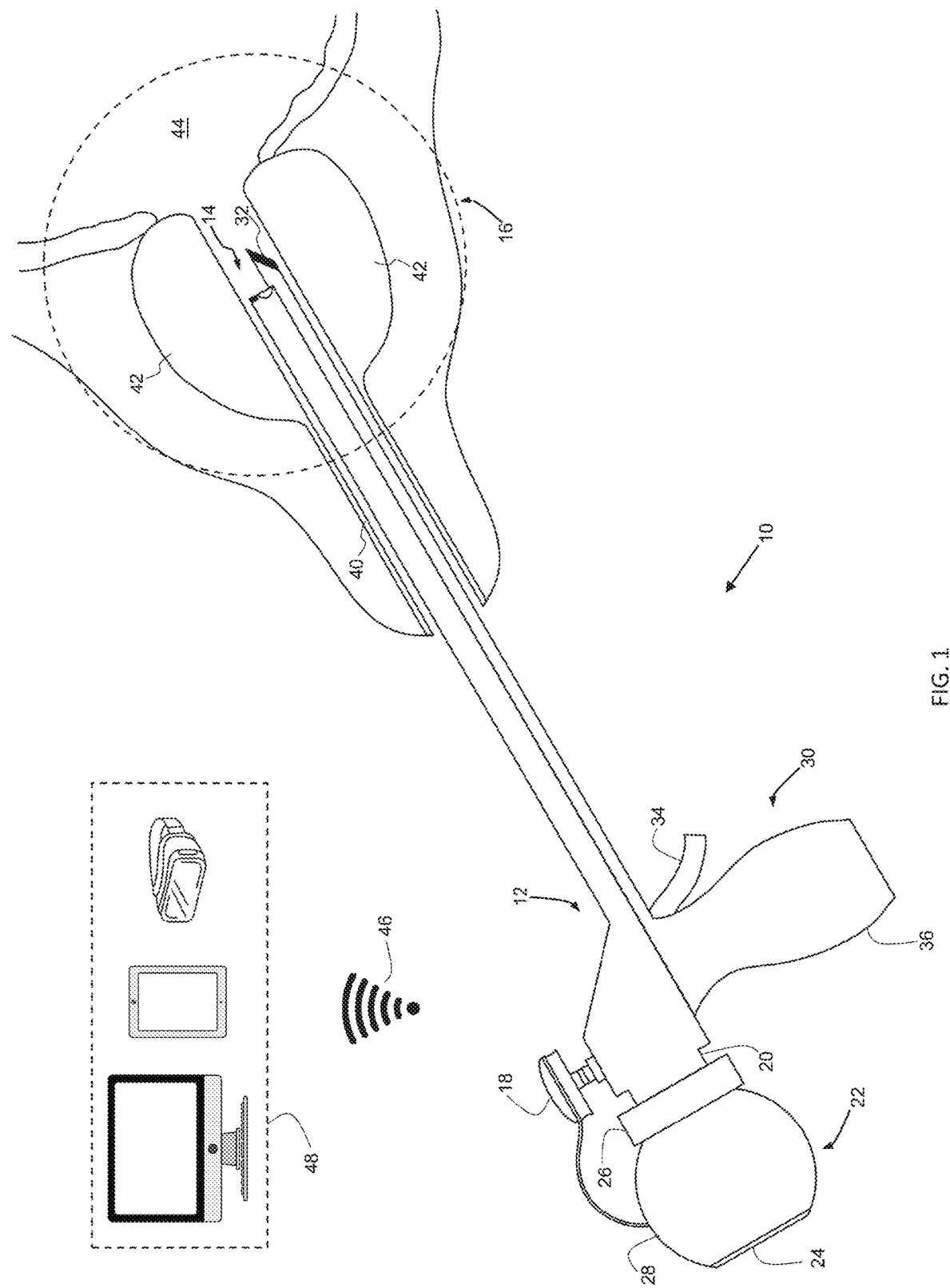
FIG. 1 is a structural diagram of an embodiment of a portable system.

Hereinafter, various embodiments of the present disclosure will be described in detail with reference to the accompanying drawings so that the present disclosure may be readily implemented by those skilled in the art. However, it is to be noted that the present disclosure is not limited to the embodiments but is capable of being embodied or carried out in various other ways. In drawings, parts irrelevant to the description are omitted for the simplicity of explanation, and like reference numerals denote like parts through the whole document.

Note that various terminology used herein can imply direct or indirect, full or partial, temporary or permanent, action or inaction. For example, when an element is referred to as being "on," "connected" or "coupled" to another element, then the element can be directly on, connected or coupled to the other element or intervening elements can be present, including indirect or direct variants. In contrast, when an element is referred to as being "directly connected" or "directly coupled" to another element, there are no intervening elements present.

Likewise, as used herein, a term "or" is intended to mean an inclusive "or" rather than an exclusive "or." That is, unless specified otherwise, or clear from context, "X employs A or B" is intended to mean any of the natural inclusive permutations, That is, if X employs A; X employs B; or X employs both A and B, then "X employs A or B" is satisfied under any of the foregoing instances.

Similarly, as used herein, various singular forms "a," "an" and "the" are intended to include various plural forms as well, unless context clearly indicates otherwise. For example, a term "a" or "an" shall mean "one or more," even though a phrase "one or more" is also used herein. For example, "one or more" includes one, two, three, four, five, six, seven, eight, nine, ten, tens, hundreds, thousands, or more including all intermediary whole or decimal values therebetween.

Moreover, terms "comprises," "includes" or "comprising," "including" when used in this specification, specify a presence of stated features, integers, steps, operations, elements, or components, but do not preclude a presence and/or addition of one or more other features, integers, steps, operations, elements, components, or groups thereof. Furthermore, when this disclosure states that something is "based on" something else, then such statement refers to a basis which may be based on one or more other things as well. In other words, unless expressly indicated otherwise, as used herein "based on" inclusively means "based at least in part on" or "based at least partially on."

Additionally, although terms first, second, and others can be used herein to describe various elements, components, regions, layers, or sections, these elements, components, regions, layers, or sections should not necessarily be limited by such terms. Rather, these terms are used to distinguish one element, component, region, layer, or section from another element, component, region, layer, or section. As such, a first element, component, region, layer, or section discussed below could be termed a second element, component, region, layer, or section without departing from this disclosure.

Also, unless otherwise defined, all terms (including technical and scientific terms) used herein have the same meaning as commonly understood by one of ordinary skill in an art to which this disclosure belongs. As such, terms, such as those defined in commonly used dictionaries, should be interpreted as having a meaning that is consistent with their meaning in a context of a relevant art and should not be interpreted in an idealized or overly formal sense unless expressly so defined herein.

Various features and aspects of the present disclosure are best understood by reference to the accompanying drawings, when considered during the course of the following discussion.

With reference to the drawings, FIG. 1 shows the main components of a portable system 10 used during an endoscopic procedure, which may be a diagnostic or therapeutic procedure (or another type of procedure whether medical or non-medical). An endoscope 12 is inserted into a patient 14 (e.g., a mammal, a human, an animal, a pet, a bird, a fish, a male, a female) to a region of interest (ROI) 16, such as a tissue, an organ, a body part, or any other in vivo feature, although non-medical uses may employ non-patients or inanimate objects, such as tubes, cavities, tunnels, crevices, bores, channels, or other relevant non-patient or inanimate ROIs. The region of interest 16 is illuminated by an external light source 18 which directs incident light along an illumination pathway, such as an optical fiber that extends along a tube of the endoscope 12 to an illumination lens at a distal tip 14. The illuminated region of interest 16 reflects the incident light back to an imaging lens at the distal tip 14 to convey the reflected light along an imaging pathway, such as an optical fiber to an observation port 20, such as an eyepiece. The reflected light is received by a wireless imaging unit (WIU) 22 via the observation port 18. The WIU 22 may include a digital imaging sensor that converts the reflected light into imaging data which can then be processed and displayed on a display 24.

In other embodiments, the endoscope 12 may be a digital endoscope with a chip-on-a-tip arrangement. For example, the endoscope 12 may include one or more light-emitting diodes (LEDs) disposed at the distal tip 14 for illuminating the ROI 16. In this arrangement, there is no external light source 18. The distal tip 14 may also include the digital imaging sensor for generating the imaging data of the ROI 16. A communication pathway along the tube of the endoscope 12 may transmit and receive control signals for controlling the LEDs and the digital imaging sensor instead of the illumination and imaging pathways. The WIU 22 may receive the imaging data from the digital imaging sensor via the observation port 20. In one embodiment, the observation port 20 serves as an optical observation port, such as an eyepiece, while in another embodiment, the observation port 20 may take the form of a digital interface, such as a digital connector for conveying imaging data electronically. The observation port 20 interfaces with the WIU 22 via an imaging coupler 26. In the illustrated embodiment, the imaging coupler 26 optically couples the WIU 22 to the observation port 20 of the endoscope 12. In the previously mentioned chip-on-a-tip embodiment, the imaging coupler 26 digitally couples the WIU 22 to a digital observation port 20 via an electrical connector with various data channels and/or electrical channels for controlling the LEDs and/or digital imaging sensor at the distal tip 14. The WIU 22 includes a housing 28 which is configured to integrate the observation port 22, display 24, imaging coupler 26, and light source 18 into a single device, while protecting various internal components, such as, but not limited to, electronic circuit components, power source, thermal management, and the like.

The portable system 10 includes a therapeutic device 30 configured to be disposed in vivo into the ROI 16 in tandem with the endoscope 12 to administer a therapy (or another action or technique) therein. For example, this may include prevention, forecasting, diagnosis, amelioration, monitoring, or treatment of medical conditions via or while the endoscope 12 is disposed in vivo into the ROI 16. As such, in those situations, the device 30 may be suitably labeled/configured (e.g., the diagnosis device 30, the forecasting device 30, the prevention device 30, and so forth). In situations that are non-medical, the device 30 is suitably configured as well. The therapeutic device 30 includes an end effector 32 which delivers the therapy (or another action or technique) and includes an actuator 34 for initiating the delivery of the therapy (or another action or technique). In the illustrated embodiment, the ROI 16 includes at least a prostatic urethra 40, the prostate 42, and the bladder 44, although this is illustrative and other body parts, organs, or tissues may be used (or inanimate ROI 16 may be used for non-medical uses). In this embodiment, the therapeutic device 30 is configured to administer therapies to treat medical conditions associated with prostatic pathologies, such as, but not limited to, benign prostatic hyperplasia (BPH) and the like, although non-prosatic pathologies may be used as well. The therapeutic device 30 may be configured to administer one or more of the following therapeutic treatments, such as resection, incision, ablation, thermotherapy, enucleation, implantation, cryotherapy, vapor therapy, embolization, and the like. While in the illustrated embodiment the therapeutic device 30 is shown with a handle 36 and actuator 34, it should be appreciated that the therapeutic device 30 may embodiment various shapes, sizes, and designs specified by the delivered therapy. For example, although the therapeutic device 30 is embodied as pistol-shaped via the handle 36, this form factor is not required and other form factors may be used. For example, the handle 36 may be omitted and the actuator 34 may be embodied differently than a lever pivoting toward or away from the handle 36 (e.g., a pressable/depressable button, a rotary knob, a rotating sleeve).

The WIU 22 is capable of wireless (e.g., radio frequency, line of sight) communication 46, such as high-speed bi-directional data communications directly (or indirectly) to one or more external devices 48 simultaneously or substantially simultaneously. The external devices 48 are capable of directly (or indirectly) receiving data, such as digital images, digital video, or other information pertaining to the therapeutic procedure. The external device 48 can also directly (or indirectly) transmit control data or signals to the WIU 22 to remotely control the WIU 22. The external device 48 can also transmit therapeutic (or other action or procedure) information regarding the therapeutic (or other action or technique) procedure, such as patient data in the form of electronic medical records (EMR) or procedure data such as instructions for performing the procedure. Examples of external devices 48 may include personal computing devices such as desktop computers; portable devices such as smart devices, smartphones, personal digital assistants, tablet computers, wrist-mounted displays, smartwatches, or the like; laptops or portable computers; head-mounted displays; or other computing devices not yet contemplated.

Figure 2:
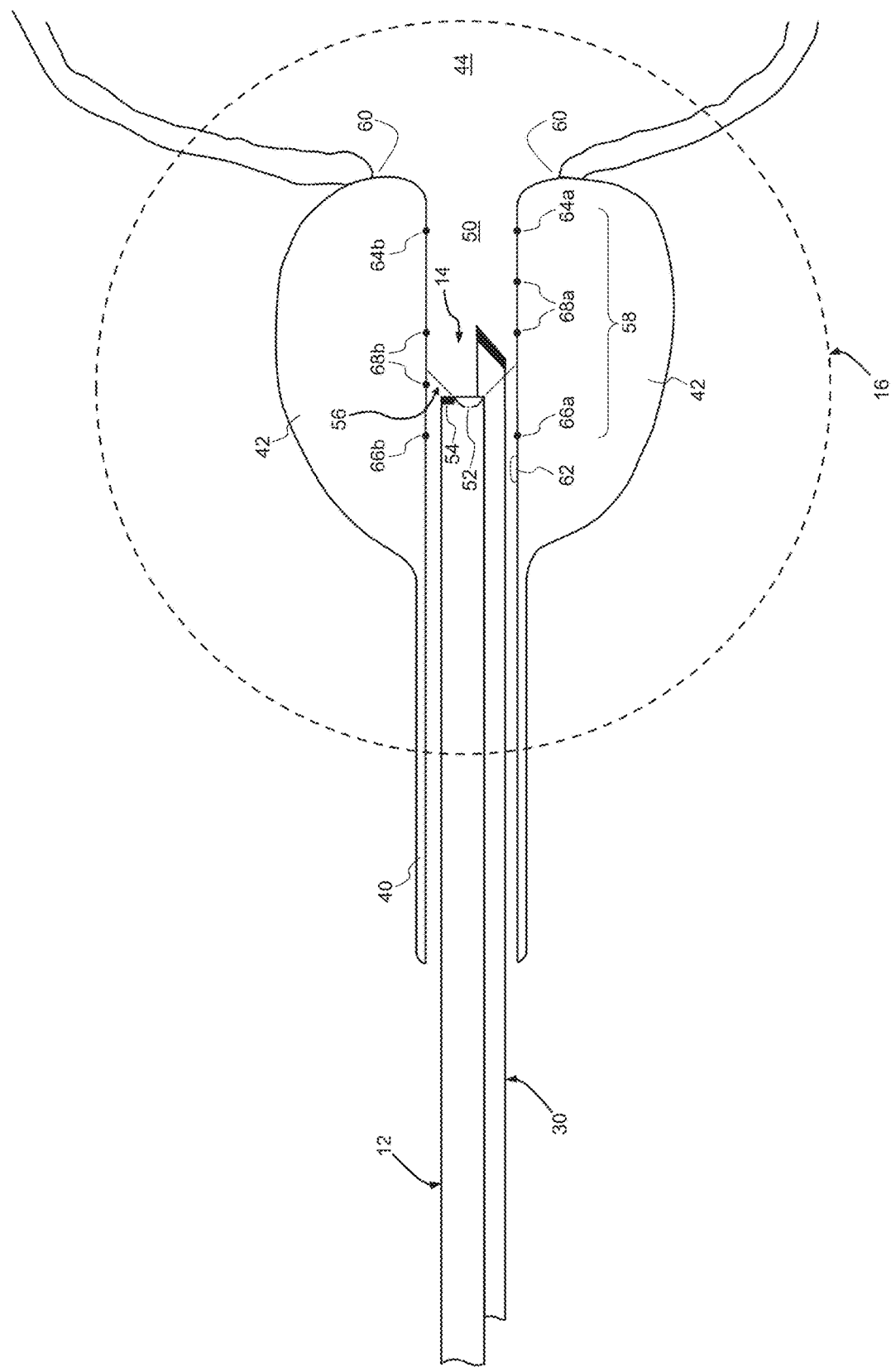
FIG. 2 is a structural diagram of an embodiment of the portable system disposed in a region of interest.

With reference to FIG. 2, an expanded view of the ROI 16 is illustrated. In an exemplary embodiment, the portable system 10 is configured for BPH therapy, although BPH or non BPH prevention, forecasting, diagnosis, amelioration, monitoring, or treatment is possible. BPH therapy typically involves reducing the effect of an enlarged prostate 42 has on the prostatic urethra 40. In the exemplary embodiment, the therapeutic device 30 is configured to deploy prostatic urethral lift (PUL) implants at various treatment sites along the prostatic urethra 40 to lift and pull prostatic tissue away from a urethral channel 50 to improve flow from, for example, the bladder 44. The locations of the treatment sites are typically chosen at the discretion of the practitioner performing the procedure based on subjective criteria, such as the degree of the achieved lifting visualized through the endoscope 12. This subjectivity may result in a non-optimal placement of the PUL implants which can result in the costly deployment of excess implants, insufficient deployment of implants such that the patient does not achieve the desired outcome, improper placement damaging sensitive anatomy such as the verumontanum or piercing through the bladder neck resulting in unintended consequences as sexual and/or bladder dysfunction, infection, and the like. Due to the subjective nature of PUL implantation, practitioners have to undergo significant training and supervision to become familiar with the procedure to perform the procedure adequately. Regardless of the training a practitioner receives, the procedure still may not be performed optimally for long-lasting results.

During a procedure, the practitioner introduces the distal tip 14 of the endoscope 12 to identify the ROI 16. The practitioner may concurrently introduce the end effector 32 of the therapeutic device 30 while identifying the ROI 16, or subsequently after the ROI 16 is identified. To identify the ROI 16, the practitioner observes real-time imaging information on the display 24 which is received by an imaging assembly 52 from the ROI 16 illuminated by incident light by a light emitter 54. The imaging assembly 46 detects reflected light from the ROI 16 within a field of view (FoV) 56 that includes at least a portion of the ROI 16 and a portion of the end effector 32 of the therapeutic device 30.

Once the distal tip 14 is situated within the identified ROI 16, the practitioner identifies a treatment region 58 between the bladder neck 60 and the verumontanum 62 so as not to damage these delicate anatomical features. The bladder neck 60 is a group of muscles that connect the bladder to the urethra and is primarily tasked with holding urine in the bladder, if damaged can lead to incontinence and other issues. The verumontanum 62 is an elevation in the floor of the prostatic urethra that is an important landmark distal which helps identify the entrance of the ejaculatory ducts.

Once identified, the practitioner retraces their movements to approximately 2 cm distal of the bladder neck 60 to a proximal treatment site 64a, 64b to achieve an adequate proximal opening. However, this proximal treatment site 64a, 64b differs greatly among patients based primarily on their specific prostatic anatomies, such as shape, size, density, and the like. If the bladder neck 60 is damaged, then such damage can lead to incontinence, bladder leakage, and other issues. If a site is chosen too proximal to the bladder neck 60, then the practitioner may pierce the bladder neck 60 and cause such dysfunction. If the site is chosen too distal to the bladder neck, then an adequate proximal opening is not achieved and symptoms of BPH, such as urinary retention and/or incomplete voiding may not be mitigated. However, even if an optimal placement is achieved at the proximal treatment sites 64a, 64b and the distal treatment sites 66a, 66b, a practitioner may also identify medial treatment sites 68a, 68b that achieve a continuous channel through an anterior aspect therebetween. Creating a channel through the anterior aspect of the prostate is typically chosen because it is generally formed of fibromuscular tissue and is generally devoid of sensitive glandular tissue. To achieve this anterior channel, additional areas of persistent obstruction are identified by the practitioner and additional implants are deployed at these medial treatment sites 68a, 68b. It may be sometimes recommended that before performing the therapeutic procedure the entire extent of the prostate should be analyzed to identify the size and shape of the patient's prostate, e.g., tall, long, short, obstructive lobes, and the like.

By visualizing the entire extent of the prostate, the practitioner can simulate the desired anterior channel. However, under certain conditions, this iterative approach can result in implantation errors when the practitioner tries to revisit these identified optimal sites without a point of reference. For example, during the initial analysis, the practitioner may note that the patient has a long prostate length and the optimal location of the proximal treatment sites 64a, 64b is 2 cm distally from the bladder neck 60; however, after revisiting these sites the practitioner may inadvertently deploy the implants 2.5 cm too distally from the bladder neck 60 and the optimal proximal opening at the bladder is not achieved. Thus, extraneous implants may have to be deployed to correct the non-optimally deployed implants.

The portable system 10 aims to minimize implantation errors by identifying and tracking various anatomical features 40, 42, 44, 60 in the ROI 16 and determining optimal treatment sites 64a, 64b, 66a, 66b, 68a, 68b based on an artificial intelligence model trained to identify anatomical features in the ROI 16 and a tracking system configured to track a motion vector of the WIU 22 and thus track the motion of the distal tip 14 of the endoscope 12 and/or the end effector 32 of the therapeutic device 30. By identifying an optimal treatment site based on a unique patient's anatomy, the therapeutic procedure can achieve enduring results while keeping costs low by increasing efficiency, reducing procedure time, and reducing non-optimal implantation errors.

Figure 3:
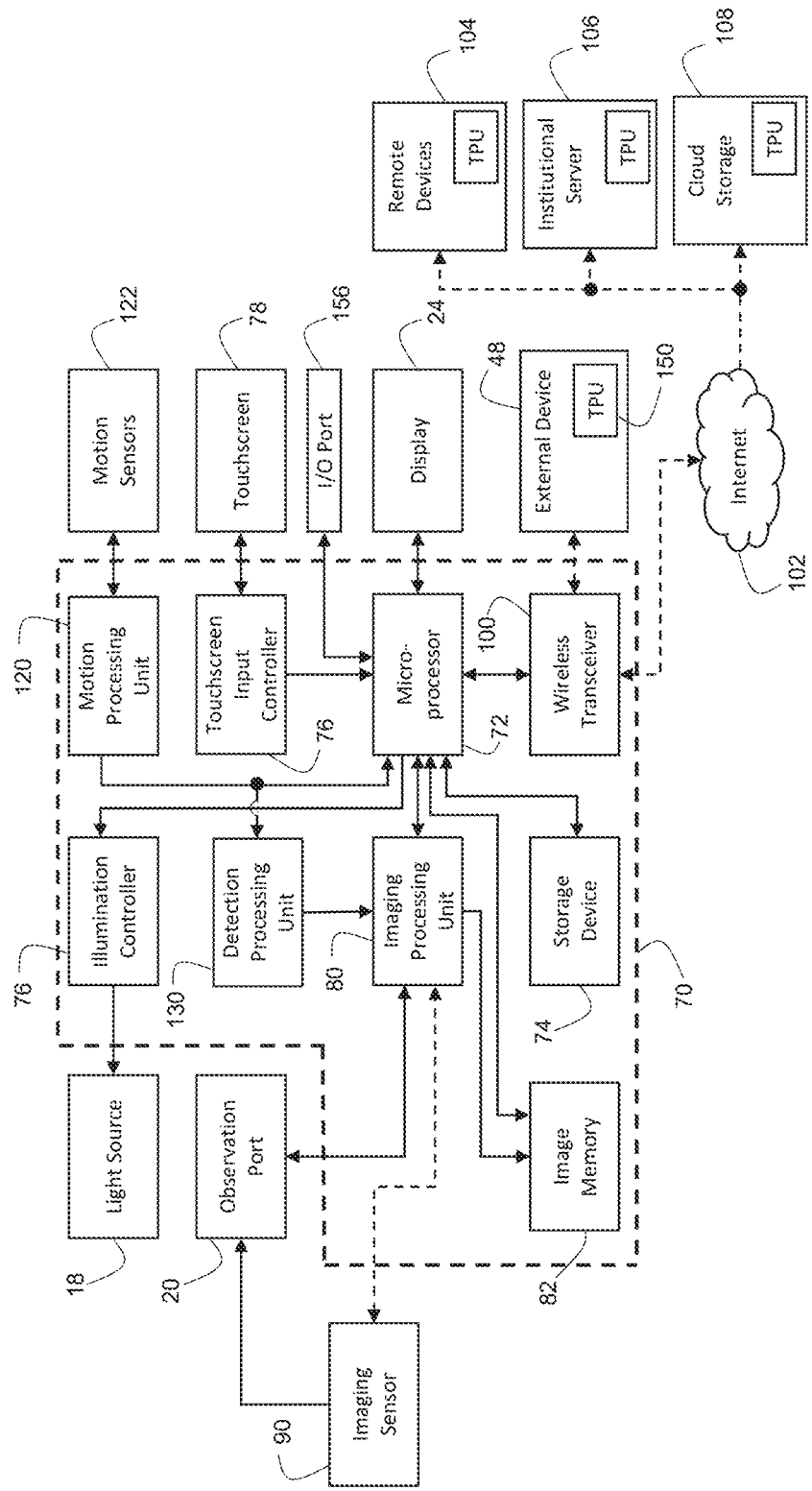
FIG. 3 is a block diagram of an embodiment of a wireless imaging unit of the portable system.

With reference to FIG. 3, a block diagram of the WIU 22 is illustrated. The previously mentioned electronic circuitry of the WIU 22 includes a system controller 70 which is configured to control and power the WIU 22. The system controller 70 includes a plurality of circuit components that are responsible for controlling aspects of the WIU 22. The system controller 70 includes a microprocessor 72 which interfaces with several electronic components to send and receive instructions to control various aspects of the WIU 22 functions. The system controller 70 includes a storage device 74 which is a memory device, such as a computer-readable medium (e.g., persistent memory, flash memory, embedded memory, ROM, RAM) for storing program instructions to be executed by the microprocessor 72. In addition to program instructions, the storage device 74 can store anatomical models, procedure data relevant to performing the therapeutic procedure, electronic medical record (EMR) related data, and the like. The system controller 70 includes a touchscreen input controller 76 configured to receive user inputs from a touchscreen 76 which is overlayed over or included within the display 24. The practitioner can interact with the touchscreen 76 to control various aspects of the WIU 22 via a user interface displayed on the display 24.

The system controller 70 also includes an illumination controller 76 which receives instructions from the microprocessor 72 to adjust the intensity or brightness of the incident light from the light emitter 54 and/or one or more frequency components of the incident light produced therefrom. It should be appreciated that the light emitter 54 may include one or more LEDs for generating incident light in the ROI 16, or it may be optically coupled to the light source 18 for transmitting incident light thereto.

An imaging processing unit (IPU) 80 may include instructions or is configured to execute instructions stored on the storage device 74 to perform various imaging-related functions. For example, the IPU 80 is configured to receive the imaging information from the imaging assembly 52 of the FoV 56. The imaging assembly 52 can be an optical assembly that directs reflected light from the ROI 16 to the observation port 22 (e.g., eyepiece) of the endoscope 12. In the exemplary embodiment, the WIU 22 includes an imaging sensor 90 integrated into the housing 28 and in direct communication with the IPU 80. In another embodiment (e.g., a chip-on-a-tip arrangement), the imaging assembly 52 comprises of the imaging sensor 90 and is disposed at the distal tip 14 of the endoscope 12. In this arrangement, the imaging sensor 90 transmits at least one of analog signals, digital signals, or a combination of analog and digital signals pertaining to the imaging information to the observation port 22 which can then be transmitted to the IPU 80.

The imaging sensor 90 may include one of the following: complementary metal-oxide-semiconductor (CMOS), charge-coupled device (CCD), or other imaging sensor devices developed in the future not yet contemplated. The imaging information can be one of a digital signal or an analog signal that is converted to a digital signal by an analog-to-digital converter (ADC) of the IPU 80 to form pixel values representing an image of a time series of the FoV 56.

The IPU 80 may also be configured to perform several image processing and post-processing functions in real-time or substantially real-time on the images of the time series. Examples of image processing techniques to enhance the images include edge detection, geometric transformations, perspective correction, color correction, color calibration, motion compensation, data compression, noise reduction, filtering, and the like. The IPU 80 may also be configured to control the functionality of the imaging sensor 90, such as adjusting a focal depth by controlling an integrated autofocus mechanism, pixel clock, sensitivity, offset, signal amplification, gain, gamma, and the like. The IPU 80 may also be configured to adjust the image size that is displayed on an external device 48 due to the difference in screen resolution and screen size between external devices 48 and the display 24. The IPU 80 may also be configured to automatically align the images such that the images are centered in the display 24 independent of the size and/or resolution of the display 24 being used whether it is the display 24 or a display of an external device 48. The IPU 80 receives the display information from the microprocessor 72 and formats the output image correspondingly. Post-processed images can then be stored on an image memory 82 for later retrieval to be viewed locally on the display 24 or the external device 102.

The WIU 22 can also be configured with a wireless transceiver 100 to communicate with the external device 48 directly via the wireless connection 46 or indirectly via the Internet 102 with remote devices 104, an institutional server 106, cloud storage system 108, and the like. However, note that the transceiver 100 can be omitted and there may be a receiver and a transmitter, or there may be a receiver or a transmitter. The remote devices 104 may be configured for viewing endoscopic imagery, video, or examination data or for remotely receiving controls and/or EMR data. The EMR data is a collection of patient and population health information electronically stored in a digital format. The EMR data may include a range of patient information such as demographics, medical history, medication, allergies, immunization status, laboratory test results, radiology images, vital signs, personal statistics, billing information, and the link. The EMR data can be stored on the institutional server 106, such as those located at a hospital, insurance company, government entity, or the like. The EMR data can also be stored on cloud storage system 88. The cloud storage system 108 can be a data storage system that includes logical pools of physical storage mediums that span multiple servers and often multiple discrete locations in a distributed fashion to ensure redundancy, fault tolerance, and durability of the data. The institutional server 106 and cloud storage system 108 can include a picture archiving and communication system (PACS) which is capable of providing storage and access to medical images from multiple modalities using a universal image format such as Digital Imaging and Communications in Medicine (DICOM) format.

It should be noted that, in some situations, the health institution server 106 and cloud storage system 88 are compliant with data protection and privacy regulation such as the Health Insurance Portability and Accountability Act (HIPAA) in the United States of America, General Data Protection Regulation (GDPR) in the European Union, Personal Information Protection and Electronic Documents Act (PIPEDA) in Canada, National Health Portal compliance set by the Insurance Regulatory and Development Authority of India (IRDAI), or other compliance regulations mandated globally.

Figure 4:
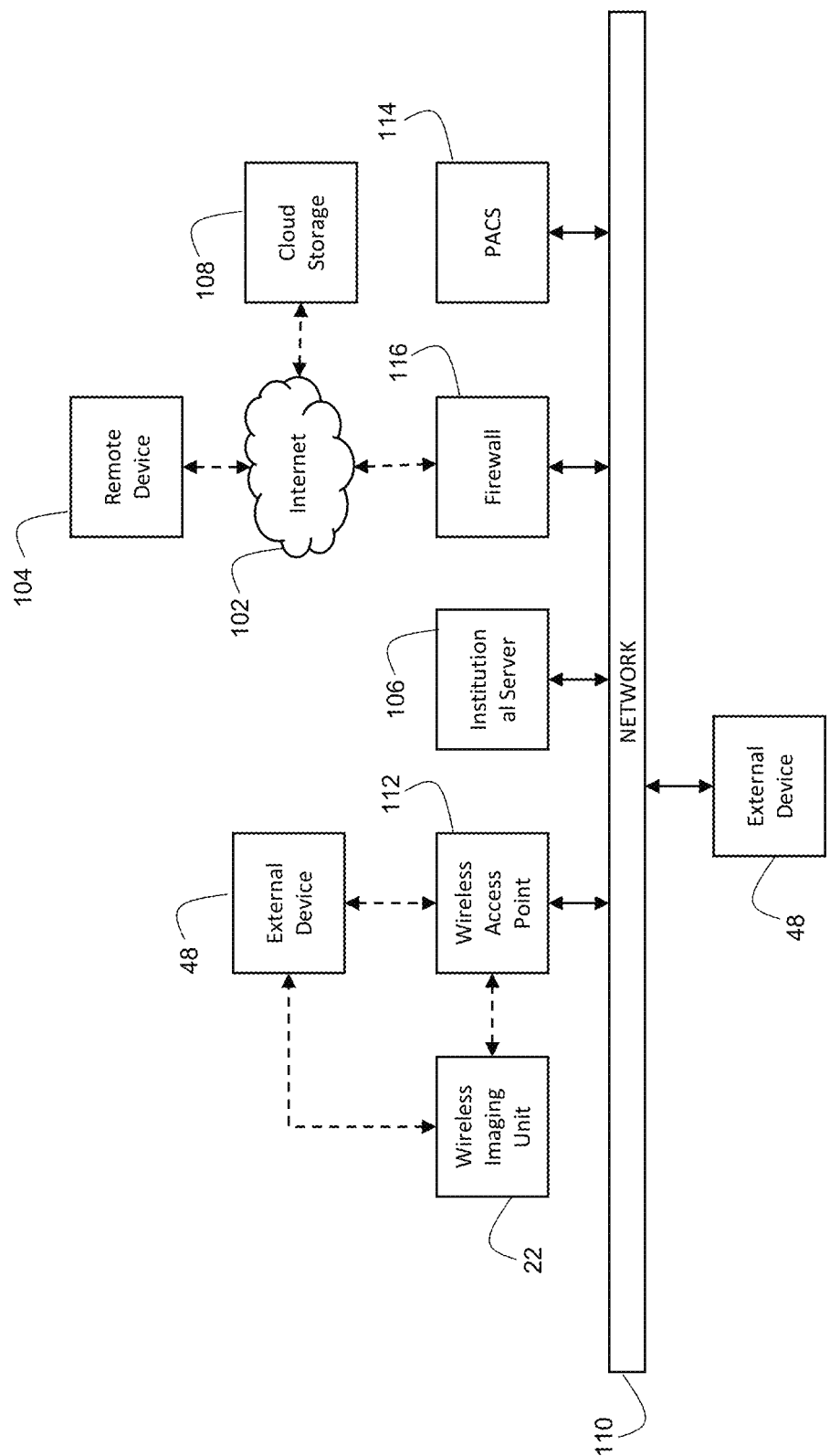
FIG. 4 a network diagram of an embodiment of the portable system is illustrated.

With reference to FIG. 4, a network diagram of an embodiment of the portable system 10 is depicted. The WIU 22 is wirelessly coupled to a local network 110 via a wireless access point 112 using a suitable wireless transmission protocol such as the 802.11 families of modulation techniques, IEEE 802.15.4a ultra-wideband (UWB), and the like (Bluetooth), although a suitable wired or waveguide connection/hardware is possible. The local network 110 may include cables, switches, and routers that may utilize Ethernet standards for communication. At least one institutional server 106 may be in communication with the local network 110. For example, the institutional server 106 may store or have access to EMR data which may be accessed by the WIU 22. Additionally, the local network 104 may be attached to a picture archiving and communication system (PACS) 114 which may be in communication with the institutional server 106 and the WIU 22. At least one external device 48 is in communication with the local network either directly via a physical connection or wirelessly via the wireless access point 112. In addition, a firewall 116 or other network security technology may be connected to the local network 110 to control access to the Internet 102. For example, a remote device 104 may be authorized to access the local network 110 via the Internet 102 utilizing a secure connection facilitated by the firewall 116. In addition, the cloud storage system 108 may be configured to store or retrieve data and may be accessed via the Internet 102 which is facilitated by the firewall 116.

With returning reference to FIG. 3, the WIU includes a motion processing unit (MPU) 120 which may include instructions or is configured to execute instructions stored on the storage device 74 to receive motion signals from a motion sensor 122. The motion sensor 122 includes at least one of a gyroscopic sensor configured to generate gyroscopic signals and an accelerometer configured to generate acceleration signals. The motion signals (e.g., the gyroscopic and acceleration signals) detect the motion of the housing 28 during the therapeutic (or another action or technique) procedure which can be used to estimate the motion of the distal tip 14 and/or the end effector 32.

The WIU 22 includes a detection processing unit (DPU) 130 which may include instructions or is configured to execute instructions stored on the storage device 74 to perform various detection-related functions. For example, these instructions may enable the DPU 130 to compare images of the time series to an artificial intelligence classifier (AIC) based on an anatomical model of the ROI 16 to classify at least one anatomical feature in each image of the series. For example, the AIC may be based on an artificial neural network (ANN), which may include a convolutional neural network (CNN), a recurrent neural network (RNN), or other suitable ANNs. For example, the storage device 74 may locally store the AIC, which may enable edge computing. This may be technologically advantageous in various environments, which may involve poor or no network connection. The exemplary embodiment, the ROI 16 includes the following anatomical features: prostatic urethra 40, prostate 42, bladder 44, verumontanum 52, and the bladder neck 60. However, other urinary tract anatomical features are also contemplated, such as but not limited to the penile urethra, membranous urethra/external urinary sphincter, bulbous urethra, median lobe, lateral lobes, ureteral orifice, ureterovesical junction, ureter, ureteropelvic junction, renal pelvis, right/left ureteral orifice, infundibulum, calyx, and the like. The anatomical features may also include pathologies, such as, but not limited to hypertrophy, trabeculations, tumors/lesions, calculus, diverticulum, and the like. Likewise, as disclosed herein, the anatomic features may or may not be anatomical, whether medical or non-medical.

The DPU 130 receives each image from the time series from the IPU 80, which may be in real-time or substantially in real-time, and compares each received image to the anatomical model, which may be in real-time or substantially in real-time, then determines a confidence metric based on the comparison, which may be in real-time or substantially in real-time. In the exemplary embodiment, the DPU includes instructions for a neural network based AIC, such as a deep learning convolutional neural network (DLCNN); however, it should be appreciated that other classifiers are also contemplated such as, but not limited to, a perceptron, a Naïve Bayes classifier, decision trees, logistical regression, K-Nearest Neighbor, a support vector machine, CNN, RNN, and the like. The AIC initially trains the anatomical model based on individual frames of previously captured times series from similar and/or adjacent ROIs. The training can be performed on the WIU 22 itself; however, the anatomical model can also be trained on an external device 48, remote device 104, institutional service 106, or the cloud storage system 108. The trained anatomical model can then be transferred to the working memory of the DPU 130 or the storage device 74 via the wireless transceiver 100. This may enable edge computing. The DPU 130 compares each image of the time series to the trained anatomical model in real-time or substantially in real-time and determines in real-time or substantially in real-time a classification for each image and a confidence metric based on the comparison. The DPU 130 is configured to instruct the IPU 80 to display, concurrently with the corresponding image, the classified anatomical features on the display 24.

The DPU 130 also receives the motion signals from the MPU 120 in real-time or substantially in real-time and determines a motion vector of the housing 28 in real-time or substantially in real-time which can then be used to estimate a motion vector of the distal tip 14 of the endoscope 12 and/or end effector 32 of the therapeutic device 30 in real-time or substantially in real-time. The motion vector can be a displacement vector, an acceleration vector, a velocity vector, a rotation vector, or the like. For example, the DPU 130 can estimate in real-time or substantially in real-time a displacement and direction of portions of the portable system 10 disposed within the ROI 16 based on the detected motion of the housing 28. The DPU 130 is configured to instruct the IPU 80 to display, concurrently with the corresponding image, the determined motion vector and/or classified anatomical features on the display 24 in real-time.

With reference to FIGS. 2 & 3, the DPU 130 can be configured to identify in real-time or substantially in real-time a treatment region 58 within the ROI 16. In the exemplary embodiment, the treatment region 58 may be a region proximal to the verumontanum 62 and distal to the bladder neck 60, thus, avoiding those delicate anatomical features. Based on the identified treatment region 58 and the classified anatomical features 40, 42, 44, 60, 62 within the ROI 16, the DPU 130 may also be configured to determine in real-time or substantially in real-time the one or more treatment sites 64a, 64b, 66a, 66b, 68a, 68b. The DPU 130 is configured to instruct the IPU 80 to display, concurrently with the corresponding image, the determined motion vector, the classified anatomical features 40, 42, 44, 60, 62, and/or the determined treatment sites 64a, 64b, 66a, 66b, 68a, 68b on the display 24 in real-time or substantially in real-time.

With reference to FIGS. 5A-5D, endoscopes views of the ROI 16 displayed on the display 24 of the exemplary embodiment of a therapeutic procedure is depicted. The practitioner will view the entire ROI 16 to classify the anatomical features 40, 42, 44, 52, 54 for the specified therapeutic procedure. The practitioner may interact (e.g., by touch) with a user interface displayed on the display 24 via the touchscreen 78 to select the desired therapeutic procedure, although a default procedure may be selected or no default procedure is selected. The DPU 130 then identifies the desired anatomical model based on the user input and retrieves the anatomical model from any one of the storage device 74, the external device 102, the remote device 104, the institutional server 106, or the cloud storage system 108. The practitioner initiates the procedure via a touch command through the user interface or by an external command by an assistant. In response, the microcontroller 72 instructs the IPU 80 to begin collecting images of the time series and instructs the MPU 120 to begin collection of the motion signals of the housing 28. The microprocessor 72 may also retrieve procedure data and/or EMR data from one of the storage device 74, external device 48, the external device 102, the remote device 104, the institutional server 106, or the cloud storage system 108 and displays the procedure data on the display 24 for the practitioner to review before commencing the procedure. The practitioner commences the procedure by introducing the portable therapeutic system into the ROI 16 to image the entirety of the ROI 16 as prescribed by the procedure data. After the anatomical features 40, 42, 44, 52, 54 are classified in real-time or substantially in real-time, the practitioner can choose whether to perform the procedure manually based on the displayed classified anatomical features 140, the displayed motion vector 142, and the displayed confidence metric 144; or the practitioner may choose to perform the procedure in a semi-automated fashion based on the determined treatment region 58 and the determined treatment sites 64a, 64b, 66a, 66b, 68a, 68b which will be described in greater detail below.

Figure 5B:
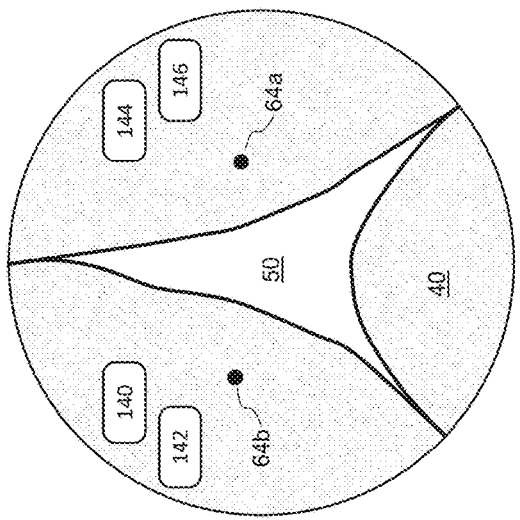
FIGS. 5A-5D endoscopic views of a region of interest as displayed on the portable system are illustrated.
Figure 5D:
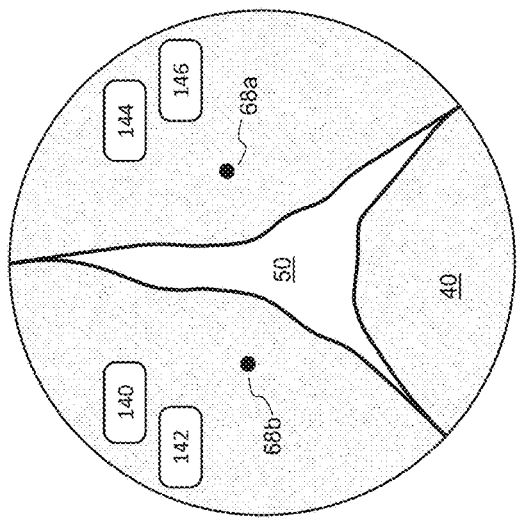
Figure 5A:
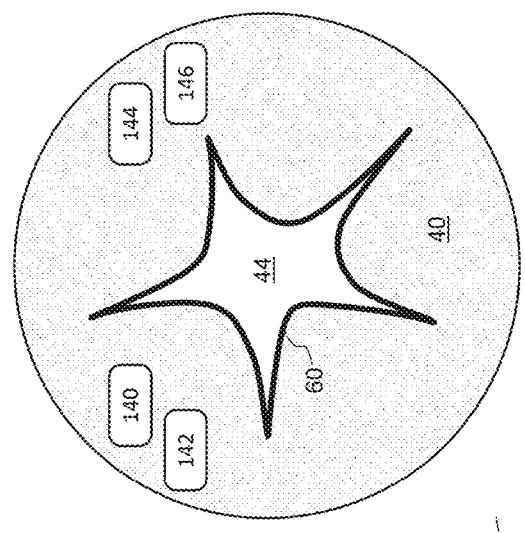

During a manual procedure, the practitioner may rely on a relative motion vector 146 such as, for example, from the bladder neck 60 to apply treatment to the proximal treatment sites 56a, 56b. The practitioner will introduce the distal tip 14 and end effector 32 into the ROI 16 till bladder 54 and bladder neck 60 is displayed as the classified anatomical feature 140 in real-time or substantially in real-time as, for example, a textual indicator indicating the corresponding anatomical feature and the displayed confidence metric 144 meets the practitioner's expectations as illustrated in FIG. 5A. The practitioner then may interact with the touchscreen 78 of the display 24 to initiate a relative motion vector 146 therefrom and retract the distal tip 14 and/or end effector 32 until the relative motion vector 146 displays an adequate displacement and/or rotation to locate an optimal location for the proximal treatment sites 64a, 64b as illustrated in FIG. 5B. The practitioner will engage the actuator 34 to deploy the treatment thereto.

Figure 5C:
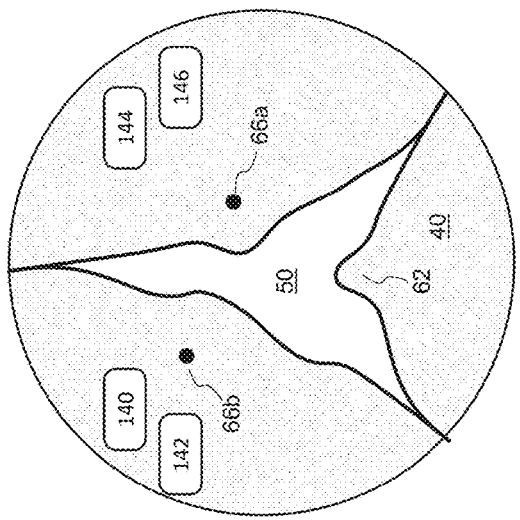

Similarly, the practitioner may repeat this process with the verumontanum 62 and the distal treatment sites 66a, 66b to deploy the treatment. After deploying the therapy at the proximal treatment sites 64a, 64b, the practitioner retracts the distal tip 14 and/or end effector 32 until the verumontanum 62 is displayed as a classified anatomical feature 140 in real-time or substantially in real-time. From there, the practitioner will protract the distal tip 14 and/or end effector 32 until the relative motion vector 146 displays in real-time or substantially in real-time an adequate displacement and/or rotation to locate an optimal location for the distal treatment sites 66a, 66b as illustrated in FIG. 5C.

Finally, the practitioner will repeat the process as necessary to apply therapy to the medial treatment sites 68a, 66b. After deploying the therapy at the distal treatment sites 66a, 66b, the practitioner protracts the distal tip 14 and/or end effector 32 along the treatment region 58 to identify regions of excess occlusion to identify one or more medial treatment sites 68a, 66b. The practitioner can rely on the relative motion vector 144 to ensure that subsequent medial treatment sites 68a, 66b are adequately spaced to achieve an optimal and continuous channel through the anterior aspect of the prostatic urethra 40 without creating unnecessary bulging adjacent to previously treated treatment sites 64a, 64b, 66a, 66b, 68a, 68b.

During a semi-automated procedure, the practitioner may rely on the automatically classified treatment region 58 and treatment sites 64a, 64b, 66a, 66b, 68a, 68b determined by the DPU 130 in real-time or substantially in real-time. After the entire ROI 16 is imaged and the anatomical features 40, 42, 44, 60, 62 are classified by the DPU 130 in real-time or substantially in real-time, the DPU 130 then determines in real-time or substantially in real-time an optimal location for the treatment sites 64a, 64b, 66a, 66b, 68a, 68b. The practitioner reintroduces the distal tip 14 and end effector into the ROI 16 until the displayed treatment site 146 is achieved in real-time or substantially in real-time with a confidence metric 144 deemed sufficient by the practitioner. Once the optimal location is achieved, the practitioner engages the actuator 34 to deploy the treatment thereto. Similar to the manual procedure, the practitioner first deploys treatment at the proximal treatment sites 64a, 64b, then the distal treatment sites 66a, 66b, and then to one or more medial treatment sites 68a, 68b until the continuous channel through the anterior aspect of the prostatic urethra 40 is achieved.

With reference to FIG. 6A, a flowchart of an embodiment of a method 200 for training the anatomical model by the DPU 130 is depicted. The images of the time series captured in real-time or substantially in real-time and classified in real-time or substantially in real-time during the therapeutic (or another action or technique) procedure are stored in the image memory 82 with corresponding classification and confidence metric metadata (or another form of data organization) as training data, S10. The training data can be used to retrain (or reinforce or update) the corresponding anatomical model. The training data is binned by the DPU 130 based on a predetermined confidence metric threshold, S12. Classified images with a confidence metric that exceeds (or satisfies) the predetermined confidence metric threshold are deemed as high confidence images and can be used to retrain (or reinforce or update) the corresponding anatomical model without further intervention. However, classified images that do not meet (or satisfy) the confidence metric threshold are deemed low confidence images and are binned for further manual verification (e.g., via a physical or virtual keyboard) by a user via the display 24 or the external device 48, the remote device 104, the institutional service 106, or the cloud storage system 108. The said devices can retrieve the low confidence images binned for manual verification from the image memory 82 via the network 104 or the Internet 102. The DPU 130 is configured to retrieve the classified images binned as high confidence images, S14, and to retrain (or reinforce or update) the anatomical models, S16. The retrained (or reinforced or updated) anatomical model is then stored on the storage device 74 for future therapeutic (or other actions or techniques) procedures, S18. It should be appreciated that the retrained (or reinforced or updated) anatomical model may also be stored on one or more of the external device 102, the remote device 104, the institutional server 106, or the cloud storage system 108 for future therapeutic (or other actions or techniques) procedures.

With reference to FIG. 3, in another embodiment, the portable system 10 includes a training processing unit (TPU) 150 disposed within at least one of the external device 102, the remote device 84, the institutional service 86, or the cloud storage system 88 that performs the retraining (or reinforcement or updating) of the anatomical model. With reference to FIG. 6B, another embodiment of a method 202 for training the anatomical model by the TPU 150 is depicted. The training data is retrieved by the TPU 150 of any one of the external device 102, the remote device 84, the institutional service 86, or the cloud storage system 88, S20. Similarly, the TPU 150 bins the images of the training data into high confidence bins and low confidence bins based on the predetermined confidence metric threshold, S22. The TPU 150 is configured to retrieve the classified images binned as high confidence images, S24, and to retrain (or reinforce or update) the anatomical models, S26. The retrained (or reinforced or updated) anatomical model is then stored on a storage device of any one of the external device 102, the remote device 104, the institutional server 106, or the cloud storage system 108 for future therapeutic (or other action or techniques) procedures, S28. It should be appreciated that the WIU 22 may retrieve the retrained (or reinforced or updated) anatomical model stored on any one of the external device 102, the remote device 104, the institutional server 106, or the cloud storage system 108 and store retrained (or reinforced or updated) anatomical model on the storage device 64 for future therapeutic (or other action or techniques) procedures.

Figure 7:
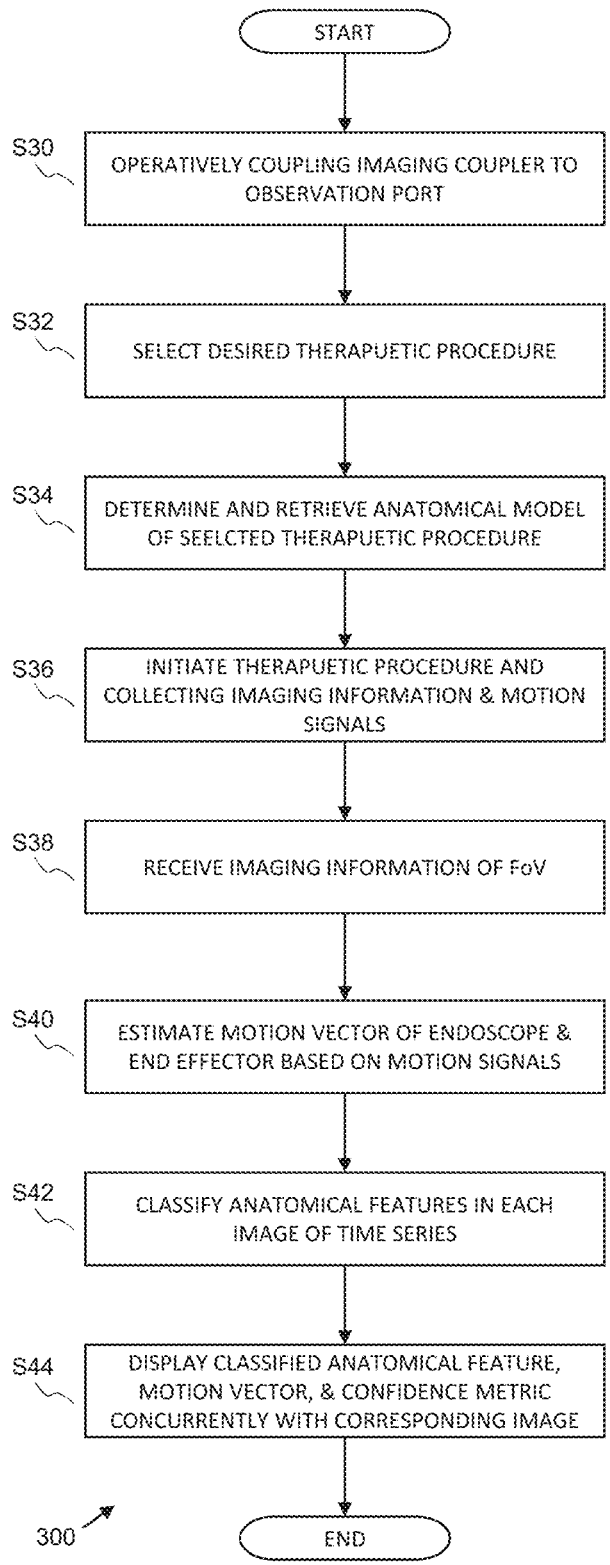
FIG. 7 is a flowchart of a method for performing an endoscopic procedure.

With reference to FIG. 7, a flowchart of a method 300 for performing an endoscopic therapeutic (or other action or technique) procedure is depicted. A practitioner (e.g., a user, a physician, a technician) operatively couples the imaging coupler 26 of the WIU 22 to the observation port 20 of the endoscope 12, S30. Via the user interface of the display 24, the practitioner selects a desired therapeutic (or other action or technique) procedure, S32. Based on the practitioner's input, the DPU 130 of the WIU 22 determines and retrieves the corresponding anatomical model of the desired therapeutic (or other action or technique) procedure from any one of the storage device 74, the external device 102, the remote device 104, the institutional server 106, or the cloud storage system 108, S34. The practitioner initiates the procedure via a touch command through the user interface and in response, the microcontroller 72 instructs the IPU 80 to begin collecting imaging information and instructs the MPU 120 to begin collection of the motion signals of the housing 28, S36. The WIU 22 receives imaging information of the FoV 56 which comprises of at least a portion of the end effector 32 of the therapeutic (or other action or technique) device 30 and a portion of the ROI 16, S38, which is converted in real-time or substantially in real-time into images of a time series and displayed in real-time on the display 24. Concurrently, the DPU 130 detects in real-time or substantially in real-time the motion of the housing 28 and estimates in real-time or substantially in real-time a motion vector of the endoscope 12 and/or end effector 32 based on the detected motion signals, S40. Based on the received imaging information and a comparison in real-time or substantially in real-time with the retrieved anatomical model, the artificial intelligence classifier of the DPU 130 classifies in real-time or substantially in real-time at least one anatomical feature in each image of the times series, S42. The DPU 130 instructs the microprocessor 72 to display, concurrently with the corresponding image of the time series, the classification of the at least one anatomical feature 140, the determined confidence metric 144, and the determined motion vector 142, S44.

Figure 8:
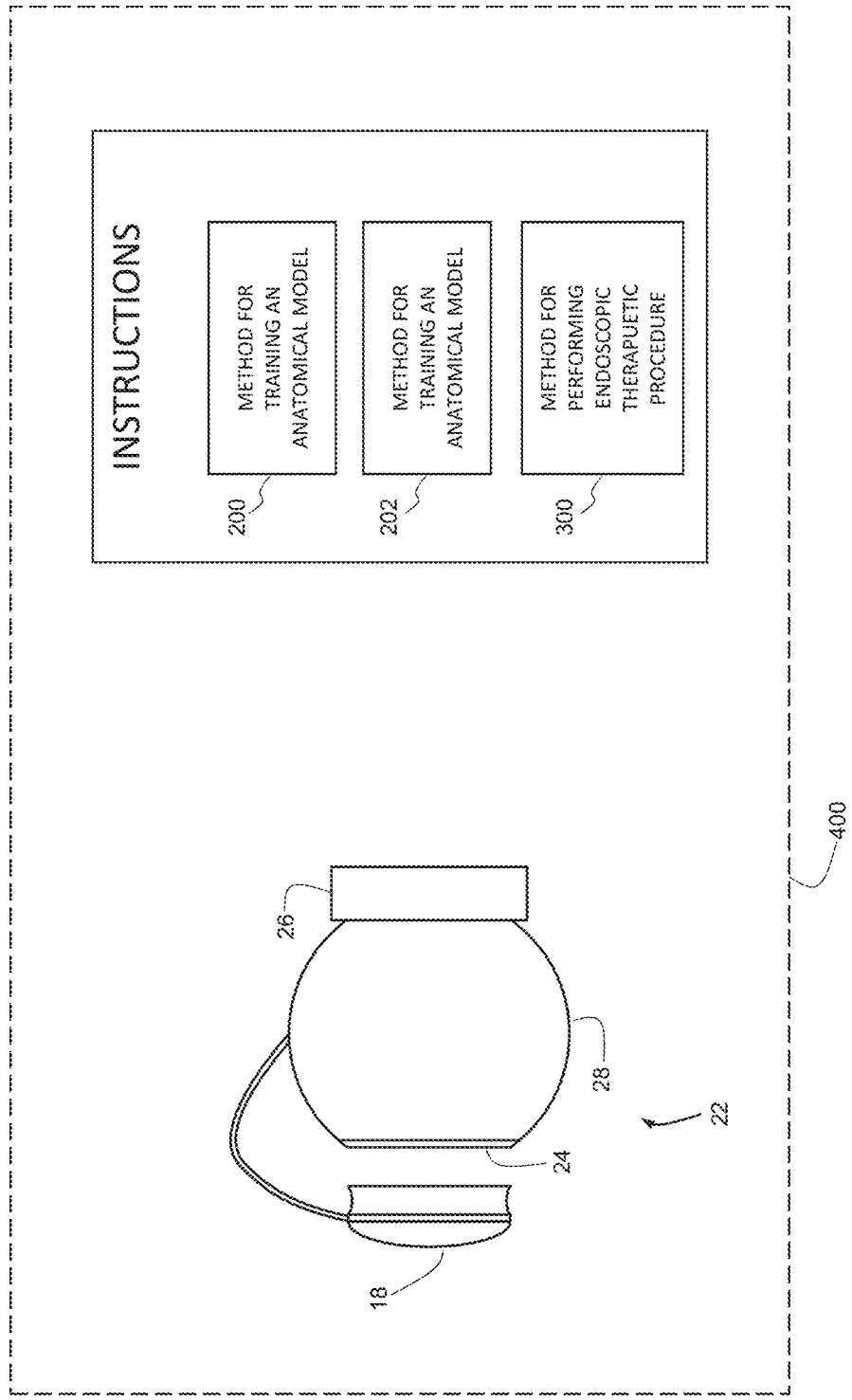
FIG. 8 is a a structural diagram of a kit for an performing an endoscopic procedure.

With reference to FIG. 8, a kit for performing an endoscopic procedure is illustrated. The kit 400 includes at least the WIU 22 according to any one of the embodiments described above and instructions 402 for performing at least one of the method 200 for training the anatomical model by the DPU 130; the method 202 for training the anatomical model by the TPU 150; or the method 300 for performing an endoscopic procedure, which, in some situations, may be an endoscopic therapeutic procedure according to or adapted to any one of the embodiments described above. For example, the kit 400 can include a container (e.g., a box, a plastic bag, a package, a case) containing the WIU 22 according to any one of the embodiments described above and instructions to perform an endoscopic procedure according to any one of the embodiments described above, whether the endoscopic procedure is medical (e.g., for prevention, forecasting, diagnosis, amelioration, monitoring, or treatment of medical conditions in various mammalian pathology) or not medical (e.g., to assist visual inspection of narrow, difficult-to-reach cavities). The container may also include at least one of the system controller 70, the light source 18, the observation port 20, the imaging sensor 90, the motion sensor 122, the touchscreen 78, the I/O port 156, the display 24, the external device 48, or others, as disclosed or not disclosed herein.

For example, the endoscopic procedure, as disclosed herein, may be used to prevent, diagnose, monitor, ameliorate, or treat a neurological condition, such as epilepsy, headache/migraine, whether primary or secondary, whether cluster or tension, neuralgia, seizures, vertigo, dizziness, concussion, aneurysm, palsy, Parkinson's disease, Alzheimer's disease, or others, as understood to skilled artisans and which are only omitted here for brevity. For example, the endoscopic procedure, as disclosed herein, may be used to prevent, diagnose, monitor, ameliorate, or treat a neurodegenerative disease, such as Alzheimer's disease, Parkinson's disease, multiple sclerosis, postoperative cognitive dysfunction, and postoperative delirium, or others, as understood to skilled artisans and which are only omitted here for brevity. For example, the endoscopic procedure, as disclosed herein, may be used to prevent, diagnose, monitor, ameliorate, or treat an inflammatory disease or disorder, such as Alzheimer's disease, ankylosing spondylitis, arthritis (osteoarthritis, rheumatoid arthritis (RA), Sjogren's syndrome, temporal arteritis, Type 2 diabetes, psoriatic arthritis, asthma, atherosclerosis, Crohn's disease, colitis, dermatitis, diverticulitis, fibromyalgia, hepatitis, irritable bowel syndrome (IBS), systemic lupus erythematous (SLE), nephritis, fibromyalgia, Celiac disease, Parkinson's disease, ulcerative colitis, chronic peptic ulcer, tuberculosis, periodontitis, sinusitis, hepatitis, Graves disease, psoriasis, pernicious anemia (PA), peripheral neuropathy, lupus or others, as understood to skilled artisans and which are only omitted here for brevity. For example, the endoscopic procedure, as disclosed herein, may be used to prevent, diagnose, monitor, ameliorate, or treat a gastrointestinal condition, such as ileus, irritable bowel syndrome, Crohn's disease, ulcerative colitis, diverticulitis, gastroesophageal reflux disease, or others, as understood to skilled artisans and which are only omitted here for brevity. For example, the endoscopic procedure, as disclosed herein, may be used to prevent, diagnose, monitor, ameliorate, or treat a bronchial disorder, such as asthma, bronchitis, pneumonia, or others, as understood to skilled artisans and which are only omitted here for brevity. For example, the endoscopic procedure, as disclosed herein, may be used to prevent, diagnose, monitor, ameliorate, or treat a coronary artery disease, heart attack, arrhythmia, cardiomyopathy, or others, as understood to skilled artisans and which are only omitted here for brevity. For example, the endoscopic procedure, as disclosed herein, may be used to prevent, diagnose, monitor, ameliorate, or treat a urinary disorder, such as urinary incontinence, urinalysis, overactive bladder, or others, as understood to skilled artisans and which are only omitted here for brevity. For example, the endoscopic procedure, as disclosed herein, may be used to prevent, diagnose, monitor, ameliorate, or treat eat a cancer, such as bladder cancer, breast cancer, prostate cancer, lung cancer, colon or rectal cancer, skin cancer, thyroid cancer, brain cancer, leukemia, liver cancer, lymphoma, pancreatic cancer, or others, as understood to skilled artisans and which are only omitted here for brevity. For example, the endoscopic procedure, as disclosed herein, may be used to prevent, diagnose, monitor, ameliorate, or treat a metabolic disorder, such as diabetes (type 1, type 2, or gestational), Gaucher's disease, sick cell anemia, cystic fibrosis, hemochromatosis, or others, as understood to skilled artisans and which are only omitted here for brevity. For example, the non-medical endoscopic procedure may be used for visual inspection work where the target area is inaccessible by other means, or where accessibility may require destructive, time consuming and/or expensive dismounting activities. For example, the non-medical endoscopic procedure may be used for in nondestructive testing techniques for recognizing defects or imperfections (e.g., the visual inspection of aircraft engines, gas turbines, steam turbines, diesel engines, automotive engines, truck engines, machined or cast parts, surface finishes, complete through-holes, forensic applications in law enforcement, building inspection, in gunsmithing for inspecting the interior bore of a firearm). In these situations above, whether medical or non-medical, the ROI 16, the model, the device 30, the implants, and relevant hardware/software and techniques of manufacture and use are adapted accordingly. Some embodiments may include a method comprising: receiving, by a processor, an imagery from an endoscope imaging a cavity, wherein the imagery depicts an anatomical feature within the cavity; performing, by the processor, a classification for the anatomical feature while the endoscope images the cavity; determining, by the processor, a confidence metric for the classification while the endoscope images the cavity; determining, by the processor, a motion vector for the endoscope imaging the cavity while the endoscope images the cavity; and requesting, by the processor, a display to simultaneously present at least two of the imagery, the classification, the confidence metric, or the motion vector while the endoscope images the cavity. The display may simultaneously present at least three of the imagery, the classification, the confidence metric, or the motion vector while the endoscope images the cavity. The display may simultaneously present the imagery, the classification, the confidence metric, and the motion vector while the endoscope images the cavity. The display may simultaneously present the imagery and at least two of the classification, the confidence metric, or the motion vector while the endoscope images the cavity. The display may simultaneously present the imagery and the classification and at least one of the confidence metric or the motion vector while the endoscope images the cavity.

Some embodiments may include a method comprising: receiving, by a processor, an imagery from an endoscope imaging a cavity, wherein the imagery depicts an anatomical feature within the cavity; performing, by the processor, a classification for the anatomical feature while the endoscope images the cavity; determining, by the processor, a confidence metric for the classification while the endoscope images the cavity; determining, by the processor, a motion vector for the endoscope imaging the cavity while the endoscope images the cavity; and taking, by the processor, an action based on the classification, the confidence metric, and the motion vector. The action may include deploying (e.g., moving, extending, adjusting, powering, grasping, cutting) an end effector within the cavity being imaged by the endoscope. For example, the end effector may be a component of a robotic arm (e.g., during a surgical procedure, an investigation of a cavity). The action may be with respect to the anatomical feature within the cavity (e.g., contacting the anatomical feature by the end effector). The action may not with respect to the anatomical feature within the cavity (e.g., another anatomical feature, an object internal to the cavity, an object external to the cavity). The cavity may be a mammalian cavity or an inanimate cavity. The action may include requesting, by the processor, a display to simultaneously present at least two of the imagery, the classification, the confidence metric, or the motion vector while the endoscope images the cavity. The display may simultaneously present at least three of the imagery, the classification, the confidence metric, or the motion vector while the endoscope images the cavity. The display may simultaneously present the imagery, the classification, the confidence metric, and the motion vector while the endoscope images the cavity. The display may simultaneously present the imagery and at least two of the classification, the confidence metric, or the motion vector while the endoscope images the cavity. The display may simultaneously present the imagery and the classification and at least one of the confidence metric or the motion vector while the endoscope images the cavity.

Various embodiments of the present disclosure may be implemented in a data processing system suitable for storing and/or executing program code that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

I/O devices (including, but not limited to, keyboards, displays, pointing devices, DASD, tape, CDs, DVDs, thumb drives and other memory media, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems, and Ethernet cards are just a few of the available types of network adapters.

The present disclosure may be embodied in a system, a method, and/or a computer program product. The computer program product may include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. The various illustrative logical blocks, modules, circuits, and algorithm steps described in connection with the embodiments disclosed herein may be implemented as electronic hardware, computer soft-ware, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending and/or flowchart illustration, and combinations of blocks in the block diagrams and/or flowchart illustration, can be implemented by special purpose hardware-based systems that perform the specified functions or acts or carry out combinations of special purpose hardware and computer instructions.

Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

Features or functionality described with respect to certain example embodiments may be combined and sub-combined in and/or with various other example embodiments. Also, different aspects and/or elements of example embodiments, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, can be at least partially performed via at least one entity or actor in any manner.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

What is claimed is:

1. A method, comprising:
receiving, by a processor, an imagery from an endoscope imaging a cavity, wherein the imagery depicts an anatomical feature within the cavity;
performing, by the processor, a classification for the anatomical feature while the endoscope images the cavity;
determining, by the processor, a confidence metric for the classification while the endoscope images the cavity;
determining, by the processor, a motion vector for the endoscope imaging the cavity while the endoscope images the cavity; and
requesting, by the processor, (a) a display to simultaneously present the imagery and at least two of the classification, the confidence metric, or the motion vector over the imagery while the endoscope images the cavity during a therapy for a benign prostatic hyperplasia (BPH) and (b) an end effector to be deployed within the cavity being imaged by the endoscope based on the classification, the confidence metric, and the motion vector during the therapy for the BPH.

2. The method of claim 1, wherein the processor requests the display to simultaneously present the imagery and the classification, the confidence metric, and the motion vector over the imagery while the endoscope images the cavity during the therapy for the BPH.

3. The method of claim 1, wherein the display is hosted by a wireless imaging unit coupled to the endoscope.

4. The method of claim 1, wherein the display is a touchscreen.

5. The method of claim 1, wherein the motion vector is determined based on a motion signal of a housing associated with the endoscope.

6. The method of claim 5, wherein the housing hosts the display.

7. The method of claim 6, wherein the display is a touchscreen.

8. The method of claim 1, wherein the imagery depicts at least a portion of the end effector.

9. The method of claim 8, wherein the motion vector is determined based on a motion signal of a housing associated with the endoscope.

10. The method of claim 1, further comprising:
requesting, by the processor, (a) the display to simultaneously present the imagery and at least two of the classification, the confidence metric, or the motion vector over the imagery while the endoscope images the cavity during at least one of a prevention, a diagnosis, a monitoring, an amelioration, or a treatment of at least one of a neurological condition, a neurodegenerative disease, an inflammatory disease or disorder, a gastrointestinal condition, a bronchial disorder, a coronary artery disease, a heart attack, an arrhythmia, a cardiomyopathy, a urinary disorder, a cancer, or a metabolic disorder, and (b) the end effector to be deployed within the cavity being imaged by the endoscope based on the classification, the confidence metric, and the motion vector during the at least one of the prevention, the diagnosis, the monitoring, the amelioration, or the treatment of the at least one of the neurological condition, the neurodegenerative disease, the inflammatory disease or disorder, the gastrointestinal condition, the bronchial disorder, the coronary artery disease, the heart attack, the arrhythmia, the cardiomyopathy, the urinary disorder, the cancer, or the metabolic disorder.

11. The method of claim 10, further comprising:
requesting, by the processor, (a) the display to simultaneously present the imagery and the classification, the confidence metric, and the motion vector over the imagery while the endoscope images the cavity during the at least one of the prevention, the diagnosis, the monitoring, the amelioration, or the treatment of the at least one of the neurological condition, the neurodegenerative disease, the inflammatory disease or disorder, the gastrointestinal condition, the bronchial disorder, the coronary artery disease, the heart attack, the arrhythmia, the cardiomyopathy, the urinary disorder, the cancer, or the metabolic disorder, and (b) the end effector to be deployed within the cavity being imaged by the endoscope based on the classification, the confidence metric, and the motion vector during the at least one of the prevention, the diagnosis, the monitoring, the amelioration, or the treatment of the at least one of the neurological condition, the neurodegenerative disease, the inflammatory disease or disorder, the gastrointestinal condition, the bronchial disorder, the coronary artery disease, the heart attack, the arrhythmia, the cardiomyopathy, the urinary disorder, the cancer, or the metabolic disorder.

12. The method of claim 1, wherein the end effector is a component of a robotic arm.

13. A system, comprising:
a processor, an endoscope, a display, and an end effector, wherein the processor is programmed to:
receive an imagery from the endoscope imaging a cavity, wherein the imagery depicts an anatomical feature within the cavity;
perform a classification for the anatomical feature while the endoscope images the cavity;
determine a confidence metric for the classification while the endoscope images the cavity;
determine a motion vector for the endoscope imaging the cavity while the endoscope images the cavity; and
request (a) the display to simultaneously present the imagery and at least two of the classification, the confidence metric, or the motion vector over the imagery while the endoscope images the cavity during a therapy for a benign prostatic hyperplasia (BPH) and (b) the end effector to be deployed within the cavity being imaged by the endoscope based on the classification, the confidence metric, and the motion vector during the therapy for the BPH.

14. The system of claim 13, wherein the processor is programmed to request the display to simultaneously present the imagery and the classification, the confidence metric, and the motion vector over the imagery while the endoscope images the cavity during the therapy for the BPH.

15. The system of claim 13, wherein the display is hosted by a wireless imaging unit coupled to the endoscope.

16. The system of claim 13, wherein the display is a touchscreen.

17. The system of claim 13, wherein the motion vector is determined based on a motion signal of a housing associated with the endoscope.

18. The system of claim 17, wherein the housing hosts the display.

19. The system of claim 18, wherein the display is a touchscreen.

20. The system of claim 13, wherein the imagery depicts at least a portion of the end effector.

21. The system of claim 20, wherein the motion vector is determined based on a motion signal of a housing associated with the endoscope.

22. The system of claim 13, wherein the processor is programmed to:
request (a) the display to simultaneously present the imagery and at least two of the classification, the confidence metric, or the motion vector over the imagery while the endoscope images the cavity during at least one of a prevention, a diagnosis, a monitoring, an amelioration, or a treatment of at least one of a neurological condition, a neurodegenerative disease, an inflammatory disease or disorder, a gastrointestinal condition, a bronchial disorder, a coronary artery disease, a heart attack, an arrhythmia, a cardiomyopathy, a urinary disorder, a cancer, or a metabolic disorder, and (b) the end effector to be deployed within the cavity being imaged by the endoscope based on the classification, the confidence metric, and the motion vector during the at least one of the prevention, the diagnosis, the monitoring, the amelioration, or the treatment of the at least one of the neurological condition, the neurodegenerative disease, the inflammatory disease or disorder, the gastrointestinal condition, the bronchial disorder, the coronary artery disease, the heart attack, the arrhythmia, the cardiomyopathy, the urinary disorder, the cancer, or the metabolic disorder.

23. The system of claim 22, wherein the processor is programmed to:
request (a) the display to simultaneously present the imagery and the classification, the confidence metric, and the motion vector over the imagery while the endoscope images the cavity during the at least one of the prevention, the diagnosis, the monitoring, the amelioration, or the treatment of the at least one of the neurological condition, the neurodegenerative disease, the inflammatory disease or disorder, the gastrointestinal condition, the bronchial disorder, the coronary artery disease, the heart attack, the arrhythmia, the cardiomyopathy, the urinary disorder, the cancer, or the metabolic disorder, and (b) the end effector to be deployed within the cavity being imaged by the endoscope based on the classification, the confidence metric, and the motion vector during the at least one of the prevention, the diagnosis, the monitoring, the amelioration, or the treatment of the at least one of the neurological condition, the neurodegenerative disease, the inflammatory disease or disorder, the gastrointestinal condition, the bronchial disorder, the coronary artery disease, the heart attack, the arrhythmia, the cardiomyopathy, the urinary disorder, the cancer, or the metabolic disorder.

24. The system of claim 13, wherein the end effector is a component of a robotic arm.

25. A non-transitory storage medium storing a set of instructions for execution by a processor to enable the processor to:
   receive an imagery from an endoscope imaging a cavity, wherein the imagery depicts an anatomical feature within the cavity;
   perform a classification for the anatomical feature while the endoscope images the cavity;
   determine a confidence metric for the classification while the endoscope images the cavity;
   determine a motion vector for the endoscope imaging the cavity while the endoscope images the cavity; and
   request (a) a display to simultaneously present the imagery and at least two of the classification, the confidence metric, or the motion vector over the imagery while the endoscope images the cavity during a therapy for a benign prostatic hyperplasia (BPH) and (b) an end effector to be deployed within the cavity being imaged by the endoscope based on the classification, the confidence metric, and the motion vector during the therapy for the BPH.

26. The non-transitory storage medium of claim 25, wherein the display simultaneously presents the imagery and the classification, the confidence metric, and the motion vector over the imagery while the endoscope images the cavity during the therapy for the BPH.

27. The non-transitory storage medium of claim 25, wherein the motion vector is determined based on a motion signal of a housing associated with the endoscope.

28. The non-transitory storage medium of claim 25, wherein the imagery depicts at least a portion of the end effector.

29. A kit, comprising:
   a processor and a display, wherein the processor is programmed to:
      receive an imagery from an endoscope imaging a cavity, wherein the imagery depicts an anatomical feature within the cavity;
      perform a classification for the anatomical feature while the endoscope images the cavity;
      determine a confidence metric for the classification while the endoscope images the cavity;
      determine a motion vector for the endoscope imaging the cavity while the endoscope images the cavity; and
      request (a) the display to simultaneously present the imagery and at least two of the classification, the confidence metric, or the motion vector over the imagery while the endoscope images the cavity during a therapy for a benign prostatic hyperplasia (BPH) and (b) an end effector to be deployed within the cavity being imaged by the endoscope based on the classification, the confidence metric, and the motion vector during the therapy for the BPH.

30. The kit of claim 29, wherein the processor is programmed to request the display to simultaneously present the imagery and the classification, the confidence metric, and the motion vector over the imagery while the endoscope images the cavity during the therapy for the BPH.

* * * * *